United States Patent
Hiromoto

(10) Patent No.: US 7,297,351 B2
(45) Date of Patent: Nov. 20, 2007

(54) PESTICIDE MICROEMULSIONS AND DISPERSANT/PENETRANT FORMULATIONS

(75) Inventor: Bryan Hiromoto, Honolulu, HI (US)

(73) Assignee: ABR, LLC, Puunene, HI (US)

( * ) Notice: Subject to any disclaimer, the term of this patent is extended or adjusted under 35 U.S.C. 154(b) by 336 days.

(21) Appl. No.: 10/773,627

(22) Filed: Feb. 5, 2004

(65) Prior Publication Data

US 2004/0161400 A1    Aug. 19, 2004

Related U.S. Application Data

(62) Division of application No. 09/826,559, filed on Apr. 4, 2001, now Pat. No. 6,720,170.

(60) Provisional application No. 60/218,968, filed on Jul. 17, 2000, provisional application No. 60/194,573, filed on Apr. 4, 2000.

(51) Int. Cl.
*A01N 65/00* (2006.01)
(52) U.S. Cl. .................................................. 424/725
(58) Field of Classification Search .............. None
See application file for complete search history.

(56) References Cited

U.S. PATENT DOCUMENTS

| | | | | |
|---|---|---|---|---|
| 3,705,855 A | * | 12/1972 | Marschner | 510/406 |
| 4,172,888 A | | 10/1979 | Delzell, Sr. | 424/166 |
| 4,521,552 A | * | 6/1985 | Schnee et al. | 523/313 |
| 4,810,507 A | | 3/1989 | Schwartz et al. | 426/33 |
| 4,863,970 A | | 9/1989 | Patel et al. | 514/784 |
| 4,975,110 A | | 12/1990 | Puritch et al. | 71/113 |
| 5,098,467 A | | 3/1992 | Puritch et al. | 71/113 |
| 5,108,457 A | | 4/1992 | Poulouse et al. | 8/111 |
| 5,200,328 A | | 4/1993 | Kirk et al. | 435/101 |
| 5,223,179 A | | 6/1993 | Connor et al. | 134/25.2 |
| 5,264,210 A | | 11/1993 | Novitski et al. | 424/93 |
| 5,362,707 A | | 11/1994 | Fiard et al. | 504/234 |
| 5,454,982 A | | 10/1995 | Murch et al. | 510/350 |
| 5,500,154 A | | 3/1996 | Bacon et al. | 510/102 |
| 5,514,588 A | * | 5/1996 | Varadaraj et al. | 435/262 |
| 5,674,897 A | | 10/1997 | Kim et al. | 514/552 |
| 5,698,592 A | | 12/1997 | Kim et al. | 514/552 |
| 5,759,974 A | | 6/1998 | Menke et al. | 510/191 |
| 5,827,522 A | | 10/1998 | Nowak | 424/405 |
| 6,048,368 A | | 4/2000 | Tcheou et al. | 8/137 |
| 6,093,681 A | | 7/2000 | Ward et al. | 504/116 |
| 6,124,359 A | | 9/2000 | Feitelson et al. | 514/552 |
| 6,387,874 B1 | | 5/2002 | Schalitz et al. | 510/530 |
| 6,391,837 B1 | | 5/2002 | Coleman | 510/238 |
| 6,399,052 B2 | | 6/2002 | Blount et al. | 424/70.5 |
| 6,475,501 B1 | | 11/2002 | Kelly et al. | 424/404 |
| 6,498,137 B1 | | 12/2002 | Schalitz et al. | 510/530 |

FOREIGN PATENT DOCUMENTS

| | | |
|---|---|---|
| EP | 0500410 | 8/1992 |
| EP | 0579052 | 1/1994 |
| JP | 57063086 | 4/1982 |
| JP | 363191802 | 8/1988 |
| JP | 02092281 | 4/1990 |
| JP | 05168480 | 7/1993 |
| JP | 08283787 | 10/1996 |
| WO | WO 97/14305 | 4/1997 |
| WO | WO 98/59036 | 12/1998 |
| WO | WO 99/14293 | 3/1999 |

OTHER PUBLICATIONS

Nerud et al., *Ceska Mykol* (1982) 36(1):45-46.
Sela et al., *Eur J Plant Pathol* (1998) 104:59-67.
Sitaramaiah et al., *Indian J Nematol* (1977) 7:58-65.

* cited by examiner

*Primary Examiner*—Michael Meller
(74) *Attorney, Agent, or Firm*—Morrison & Foerster LLP

(57) ABSTRACT

A clear aqueous emulsion of a complex comprising a moiety having a hydrophilic core to which is covalently bound the backbone of at least one monounsaturated $C_{16}$-$C_{20}$ fatty acid and appropriate surfactants is effective in controlling agricultural pests, including nematodes.

11 Claims, No Drawings

PESTICIDE MICROEMULSIONS AND DISPERSANT/PENETRANT FORMULATIONS

CROSS-REFERENCE TO RELATED APPLICATIONS

This application is a divisional of U.S. Ser. No. 09/826,559 filed 4 Apr. 2001 now U.S. Pat. No. 6,720,170 and now allowed which application claims priority under 35 U.S.C. § 119(e) from U.S. provisional application Ser. No. 60/194,573 filed 4 Apr. 2000 and U.S. provisional application Ser. No. 60/218,968 filed 17 Jul. 2000. The contents of these applications are incorporated herein by reference.

TECHNICAL FIELD

The invention relates to agricultural pest control. More specifically, the invention concerns use of natural product derived microemulsions to control agricultural pests, in particular plant nematodes.

BACKGROUND ART

The negative impact of infestation by pests on agricultural production is well-known. Damage worldwide due to nematode infestation alone is estimated at $78 billion per year. Other sources of infestation include bacterial, fungal, and insect pathogens. Assault on these infestations has taken the form of use of synthetic pesticides derived from petroleum, use of natural predators, and use of compounds derived from natural sources, such a pyrethrins. No completely satisfactory pesticide which is specific, effective, and not harmful to the environment has been found. Thus, there is a considerable need for finding improved pesticides.

With regard to previous compositions related to those of the present invention, the effect of fatty acids on a particular species of plant nematodes (*Meloidogyne javanica*) has been described by Sitaramaiah, K., et al., *Indian J. Nematol.* (1977) 7:58-65. Formic, acetic, propionic and butyric acids were tested. The effect of a collagenolytic/proteolytic enzyme secreted from *Bacillus cereus* after induction by collagen on this plant nematode species has also been reported by Sela, S., et al., *Eur. J. Plant Pathol.* (1998)104:59-67. The enzyme was effective to digest collagen from cuticles of second stage juveniles. U.S. Pat. No. 5,698,592 describes compositions for the control of plant infective nematodes using fatty acid compounds which compositions are microemulsions containing $C_8$-$C_{14}$ fatty acid esters. The esters were prepared synthetically and the nature of the microemulsions is not described.

Fatty acid or oil compositions have also been described for other purposes, including the use of a vegetable oil/mineral salt broth fermented by yeast as an emulsifier in the food industry, as described in U.S. Pat. No. 4,810,507; the use of a mixture of an oleate derivative, a lower alkanol, and an inert diluent as a pharmaceutical penetration agent, as described in U.S. Pat. No. 4,863,970; and the use of a solution of oleic acid, acetone, and ammonium hydroxide in water as a treatment for athlete's foot, as described in U.S. Pat. No. 4,172,888. Unsaturated lipid compounds containing polar head groups, including oleates, are described as cell-envelope disordering compounds.

The use of microbial infection to control nematode infestation in plants was described in U.S. Pat. No. 5,264,210. PCT Application WO98/59036 describes compositions for the control of nematode infestation using metabolites from fungi. In some cases, the fungi are cultured in media which include vegetable oil and the compositions may include surfactants.

U.S. Pat. Nos. 5,674,897; 5,698,592; and 6,124,359, all assigned to Mycogen describe microemulsions containing fatty acid esters for use as nematocides. These fatty acid esters are of $C_8$-$C_{14}$ fatty acids and they do not appear to include glyceride esters. Various other patents disclose the use of alkoxylated materials and other emulsifiers for use in pesticides or herbicides intended for application to plants. These include U.S. Pat. Nos. 4,975,110 and 5,098,467 to Safer; U.S. Pat. No. 5,827,522 to Troy and U.S. Pat. No. 6,093,681 to Monsanto. In addition, U.S. Pat. No. 5,362,707 assigned to Rhone Poulenc describes the use of "suspoemulsions" as vehicles to apply pesticides with solid active ingredients (having melting points >45° C.) to plants.

It has not heretofore been appreciated that complexes containing a hydrophilic core, at least one monounsaturated fatty acid backbone, surfactants, and including a polyalkoxylene, (such as compositions containing a denatured lipase with long chain fatty acids or their derivatives) prepared in the form of a clear microemulsion are particularly effective in controlling pests in agricultural settings.

In addition, the formulation of agents employed for dispersal and penetration of active ingredients is useful as a carrier for plant nutrients, pesticides in general, herbicides, and other materials suitable for application to plants and is also useful as a topical drug delivery system.

A wide variety of carriers for active ingredients has been devised in both the pharmaceutical and agricultural arts. For example, drug delivery systems have included various forms of liposomes, various polymeric slow-release compositions, detergents which aid in penetration, and other excipients that affect the behavior of small molecules or proteins or other biological molecules that are considered to be the active ingredients. The formulation of the present invention, originally developed as a carrier for nematocides, has been found useful as a delivery system for pesticides in general, for plant nutrients, and for topical application of drugs as well. The carrier of the present invention is particularly effective in dispersing active ingredients over a wide area and in effecting penetration of these active ingredients through cell walls and membranes and is thus useful both in agricultural and pharmaceutical contexts.

DISCLOSURE OF THE INVENTION

The invention is directed to environmentally friendly but effective pesticides for use on plants. The pesticide can be prepared in a premixed concentrated form and then diluted for application to agricultural crops such as tomato, potato, pineapple, and any other target crop which is subject to pest infestation. The composition is a microemulsion that appears clear to the naked eye. Indeed, the turbidity of the microemulsion must be quite low—when measured with a turbidometer, the turbidity should be less than about 3 NTU, preferably less than 2.5 NTU, more preferably less than 1 NTU. The clear microemulsion will contain as active ingredient a complex which comprises a moiety having a hydrophilic core to which is covalently bound at least one backbone of a monourisaturated fatty acid of $C_{16}$-$C_{20}$, preferably an oleic acid backbone. As used herein, "backbone" of a fatty acid refers only to the carbon chain and does not include the carboxyl group oxygens. Typically, this core is a saccharide, such as sucrose, glucose, or a more complex saccharide esterified with one or more oleic acid or similar residues. The complex moiety may also be formed from the association of a denatured lipase and a long chain monounsaturated fatty acid or its esters. The complex will also contain detergents and some form of polyoxyalkylene, such as polyoxyethylene. The polyoxyalkylene may be associated directly with the moiety described above or may be included in a separate portion of the complex.

Thus, in one aspect, the invention is directed to the active ingredient of the pesticide, which is a complex consisting essentially of at least one $C_{16}$-$C_{20}$ monounsaturated fatty acid or ester thereof associated with a denatured lipase, an anionic surfactant blend, a microemulsion surfactant blend, and polymers which are polyoxyalkylene polymers. The polyoxyalkylene is supplied by providing alkyoxylated linear alcohols of $C_9$-$C_{11}$. In another embodiment, the active ingredient is a complex consisting essentially of a saccharide esterified with at least one monounsaturated $C_{16}$-$C_{20}$ fatty acid and the anionic surfactant blend, a microemulsion surfactant blend, and polymers which are polyoxyalkylene polymers. The polyoxyalkylene polymers are preferably provided by derivatizing the saccharide.

In another aspect, the invention is directed to a pesticide premix consisting essentially of a homogenized mixture of the components set forth above. Further, the invention is directed to the diluted form of the premix and to a method to control agricultural pests which comprises applying the pesticidal dilution to an agricultural crop.

The invention is further directed to methods to prepare these pesticide compositions.

Specifically, the carrier comprises at least three components. The first component is at least one linear alcohol of 7-12C, preferably 9-11C, which is polyalkoxylated. The second component is at least one surfactant which is designed to promote formation of microemulsions. The third component is at least one anionic surfactant. If desired, a disproportionate amount of a linear alcohol of 11-12C with a high degree of polyalkoxylation may also be included. The components should be mixed in a particular order in order to ensure maximum effectiveness.

Thus, in another aspect, the invention is directed to a dispersant/penetrant which consists essentially of:
at least one linear alcohol of 7-12C which linear alcohol is polyalkoxylated;
at least one surfactant that promotes microemulsion; and
at least one anionic detergent.

The invention is also directed to agricultural and pharmaceutical compositions which comprise at least one active ingredient (for example, the nematicide complex described above) and the dispersant/penetrant compositions of the invention. In still another aspect, the invention is directed to methods to prepare and use these formulations.

Modes of Carrying Out the Invention

The pesticide compositions of the invention are applied to crops or to fields or environments where pesticide control is desired in the form of clear microemulsions. The clarity appears to be important. Not only does the final composition need to appear clear to the naked eye, it should have a very low turbidity index when measured in a turbidometer. Preferably, the composition should be less than 3 NTU, more preferably less than 2.5 NTU, and still more preferably less than 1 NTU. Pure water has an NTU value of 0.3.

The compositions ultimately to be applied are prepared by diluting a premix which contains the active ingredient.

While not intending to be bound by any theory, it is believed that the active ingredient in the pesticide compositions in the invention is a complex comprising a moiety containing a lipophilic component and a hydrophilic portion which can be associated with an anionic surfactant. There are two embodiments of the active ingredient which share these characteristics.

Lipase/Fatty Acid Complexes

In one embodiment, lipases which can complex with triglycerides comprising fatty acids which contain a single double bond and which have maximal activity on fatty acid chain lengths of 8 carbons are employed. These have minimal enzymatic effects on esters of $C_{18}$ fatty acids. In a preferred embodiment, the fatty acids which are present in the complexes of the present invention may have chain lengths of 16-20 carbons. More preferably, the chain length of the triglyceride-esterified fatty acid used in the composition is $C_{18}$. The lipase may merely associate with the triglyceride and not hydrolyze it; indeed, in some compositions of the invention prepared from oils comprised primarily of oleate triglycerides, compositions which contain lipases derived specifically from *Laetiporus sulphureus* contain the same level of triglyceride as untreated oils. Moreover, lipases suitable for the compositions of the invention associate not only with triglycerides, but also with diglyceride and monoglyceride and other esterified forms of the fatty acids as well as with the free fatty acids themselves, provided they include fatty acids of 16-20, preferably 18 carbons in length.

Many of such lipases are of fungal origin. Since triolein is the primary storage oil of many fungi, certain fungal lipases are genetically designed not to degrade the naturally occurring triolein in the environment, but catalyze the degradation of other triglycerides with different fatty acid chain lengths. This would result in intact triolein, diolein, monolein and oleic acid in the environment of a fungal colony producing this type of lipase enzymes on a mixed fatty acid source. This type of lipase is relatively specific for 8-carbon fatty acids and will only hydrolyze $C_{18}$ fatty acids to a limited extent. The enzyme attaches to the triglyceride containing oleic acid, recognizes the chain length, and releases the triglyceride only when suitable cleavable triglyceride is available. If not, the lipase will remain attached to the uncleavable triglyceride. Thus, when these lipases are coupled with a triglyceride consisting of $C_{18}$ fatty acids, the lipase will attach, but not cleave the fatty acids from the glycerol.

It will be noted that in this embodiment, the hydrophilic core includes the oxygens of the carboxyl groups of the fatty acid residue; thus, the "backbone" of the fatty acid is covalently bound to the hydrophilic core, which includes these oxygens as well as the lipase.

In order to stabilize the complex, it is preferred that the lipase portion of the complex be denatured. Thus, the complex, after formation, is treated, preferably by heating to a suitable temperature, to denature the lipase protein.

The complex can be prepared by utilizing purified preparations of suitable lipases preferably but not necessarily derived from fungal sources and permitting the lipase to associate with a fatty acid or fatty acid ester wherein the fatty acid backbone has the appropriate length ($C_{16}$-$C_{20}$) and the preferred amount of unsaturation (one double bond). The ester may be an ordinary ester such as a methyl, ethyl, ethylene glycol, propyl, or butyl ester, and the like, or, preferably, the fatty acid is esterified to glycerol either as a mono, di and preferably triglyceride. Triglycerides are readily available as components of vegetable oils, and thus vegetable oils constitute a preferred source, especially oils that contain high concentrations of trioleate, such as safflower or sunflower seed oil.

The complex, for use in the compositions of the invention must be denatured. The denaturation step is typically performed by heat, but other denaturing agents, such a chaotropic agents and adjustment of pH could also be used. The denaturation step is an essential one in preparing the resultant hydrophobic/hydrophilic complex.

Thus, for preparing these compositions, a vegetable oil, high in trioleate content is preferred. Such an oil is, for example, Optimum™ Sunflower Oil, Optimum Quality Grains, Inc., Urbandale, Iowa. Other oil compositions which contain mono, di, or triglycerides of fatty acids of suitable length may also be used. The presence of a single double bond in the fatty acid is preferred. It should be emphasized that the trioleate must contain at least one monounsaturated fatty acid of 16-20 carbons in length, preferably 18 carbons, but this need not be the only fatty acid component of the oil. As long as substantial amounts of this fatty acid are present.

Oil sources include nonplant sources such as from fish or whales which would increase the carbon chain possibilities for monounsaturates from a range of $C_{16}$ - $C_{20}$ to $C_{16}$ - $C_{26}$. For forming the complex, suitable lipases can be obtained from plant, fungal, bacterial, and animal sources. One suitable lipase is wheat germ lipase. (Wheat germ lipase does not digest triolein.) Suitable fungi include *Laetiporus sulphureus, Ganoderma* spp, *Mucor* spp, *Rhizopus* spp, and *Penicillium* spp. Also available are lipases from fungi such as *Candida* spp and *Aspergillits* spp. Suitable bacteria include *Pseudomonas* spp, *Rhizobium* spp or *Chromobacteriuzm* spp. Suitable animal sources include pigs, goats, sheep, and bovine sources. Lipases are also commercially available such as those obtainable from Valley Research Technologies, South Bend, Ind., which markets Validase 8000, a lipase commonly used in cheese-making. Of course, mixtures of individual lipases can be used. Typical lipases useful in the invention are those described by enzyme No. ECC 3.1.1.3 or CAS No. 9001.62-1.

A wide variety of lipase sources can thus be used. One such source is cheese itself and the various microorganisms used in its manufacture. It should be emphasized that because many cheeses have a high lipase content, such cheeses can be used in the formulation per se. The types of cheese that can be used constitute a wide variety, including cottage cheese, cream cheese, brie, mozzarella, Monterey Jack, Munster, blue cheese, cheddar, edam, gouda, Swiss, parmesan and romano. Particularly preferred is chevre which has a high moisture content and appears to be very high in lipase content, especially when fresh. Blue cheese and brie also have high contents of lipase. The bacteria and fungi that are used in the manufacture of these cheeses also are good lipase sources. These microorganisms include, prominently, *S. lactus, S. cremoris,* and *S. thermophilus.*

In addition to these microorganisms, the ATCC web site provides an extensive list of microorganisms including many *penicilia* and *kluyveromyces* that produce lipase. There is an extensive list of fungi in general, and yeast in particular that produce lipase that is useful in the invention. Such organisms include *Aspergillus oryzae, Aspergillus soyae, Sachromyces rouxii, Aspergillus flavus, Hansenula subpelliculosa, Zygosachromyces, Lactobacillus delbraeki, Rizous oligosporus, Neuraspura sitophila,* and many others. In addition, a wide variety of yeasts, as listed in the American Type, Culture Collection Catalog, current edition, incorporated herein by reference, lists multiple yeast genera which can be used as sources of lipase.

Finally, lipases are found in seeds of germinating plants, such as wheat, oats, corn, rice and rye, as well as plants where seeds contain substantial amounts of triglycerides, such as soy beans, safflower, canola, corn, cotton seed, sunflower, olive, walnuts, macadamia nuts, peanuts, and the like can be used as a source of lipase. Crude extracts can be used or the lipase can be purified to any desired extent. In these preparations, other stabilizing components, such as dextrin, may be included.

In general, the ester and lipase are mixed together in an aqueous environment for a sufficient time and at an appropriate temperature to permit complex formation. Typically, complex formation occurs over a period of several hours at slightly elevated temperatures. Typical conditions would be represented by periods of 10-40 hours at temperatures of 30-50° C. Then the oil phase is recovered and subjected to treatment to denature the lipase, typically treatment using heat. Denaturing conditions vary depending on the components utilized, but typically such-conditions would include treatment at 90-99° C. for 5-20 minutes. In one manner of performing this step, the lipase is purified.

In one embodiment, to prepare the lipase/fatty acid or ester complex, above, the lipase may be supplied in the form of a culture filtrate from cultivation of a suitable fungus, such as those set forth above as suitable sources for the lipase. In this approach, the fungus is cultivated for a period of 10-30 days, preferably around 20 days, in a cultivation vessel forming a mycelium mat. Suitable nutrients are those typically appropriate for the cultivation of the particular species of fungus employed. After the incubation period, the culture fluid is separated from the mycelium. The separation may occur when the fungus is "immature" i.e., prior to the termination of growth phase or when the fungus is "mature"—i.e., at the point where growth phase begins to level off. The culture fluid is filtered and then mixed with the oil (or other fatty acid ester) for an appropriate time period, such as 18-30 hours, preferably around 24 hours at 27-35° C., preferably 33° C. After this incubation period, the oil phase is separated and the enzyme complex is denatured preferably by heat. Typical times and temperatures are 20 minutes at 100° C. or until the emulsion clears. Any particles which remain are filtered off.

When a purified lipase is used, an aqueous solution of the lipase is mixed with a suitable oil and the mixture is homogenized using starting at high speed (i.e. 30,000 rpm) or other means of homogenization such as mixing in a blender or sonication. A Power Gen Homogenizer Model 1700 with a variable speed range of 10,000 -30,000 rpm is available from Fisler Scientific. In this step, the ratio of the lipase or lipase mixture to the oil is important. If Validase 8000 fungal lipase is employed, 2 gm of the enzyme is mixed with 600 ml of water and stirred for 1 hour. The resulting enzyme solution is then added to 1 liter of sunflower oil, high oleic type, Optimum Quality Greens, LLC, Urbandale, Iowa, in a typical procedure. As set forth above, it appears that an optimum condition is a simple complex between the triglyceride and the lipase. The homogenized mixture is then incubated for a time and at a temperature sufficient to assure the association of the fatty acid or fatty ester components of the oil with the lipase. Typically, the incubation period is from 10-30 hours, preferably 15-27 hours, most preferably 24 hours and the temperature is elevated above room temperature, preferably 25-50° C., more preferably 30-45° C., and most preferably 40° C. Optimum conditions appear to be 24 hours at 40° C. Alterations of the incubation time and temperature are, however, possible since the time and temperature factors are interdependent.

After a suitable incubation period, the oil phase is separated and treated to denature the enzyme and stabilize the complex. Typical denaturation procedures include heat, typically at 95° C. for about 10 minutes. Other denaturation procedures may, however, be used, such as microwaving, pH adjustment and chaotropic agents. During heat denaturation, the emulsion clears. The denaturation is necessary to prevent enzymic activity with respect to the linear alcohols that will be added later. Heat denaturation also removes water from the lipase structure. Water interferes in the surfactant addition performed later in the formulation. Further, the lipase will no longer be able to attach to new substrate. The emulsion separates into an oil and water bi-layer; the oil layer is retained and the water layer discarded. The water layer does not form an emulsion with new oil due to the heat denaturation process.

Once the denatured complex is stabilized, any solid particles that are present are removed by centrifugation or filtration or any other effective procedure. There may be no solid particles in some instances. Surfactants are then added to complete the formation of the active complex.

Saccharide/Fatty Acid Molecules

In another embodiment of the active ingredient, the complex comprises a saccharide, such as sucrose, sorbitol, xylitol, glucose, raffinose, or erythritol esterified to at least one fatty acid residue which is monounsaturated and contains 16-20C, preferably 18C (i.e., oleic acid). The saccharide core may be esterified to one or more than one, such as 2, 3, 4 or 5 fatty acids. At least one of the fatty acids must be of the appropriate size and unsaturation; as long as this is the case, other types of fatty acid backbones may also be included. It is preferred that the polyol saccharide cores be also derivatized with polyoxyalkylenes, in particular, polyoxyethylene. In addition to saccharide cores, other alcohols may also be used, such as glycerols, which may contain polyoxyalkylene chains as well. For example, ARCO Chemicals has commercialized esterified propoxylated glycerols. The Olestra™ products of Procter and Gamble are sucrose polyesters containing fatty acids in the range of 8-22 carbons; to the extent that oleates or monounsaturated fatty acids in the $C_{16}$-$C_{20}$ range are included among these, these moieties are also useful in the invention. Particularly preferred is the commercially available material Toximul SEE-340, a sorbitan trioleate ethoxylate containing 20 moles of ethylene oxide. It may be advantageous, in this instance, to solubilize the Toximul SEE-340 initially in a mixture of aromatic hydrocarbons such as Exxon Aromatic 100. Other sorbitol esters and sorbitol ester ethoxylates can also be used. These are commonly referred to as SPANs, TWEENs, sorbac and polysorbac.

Addition of Surfactants

While not intending to be bound by any theory, in both embodiments above, it is believed that the long chain hydrophobic portion of the complex penetrates the lipid layers of the cells or membranes of the target pest, while the hydrophilic portion, preferably associated with an anionic detergent, becomes attached to the proteins embedded in the lipid layers. The effect is believed to be enhanced by the presence of shorter chain alcohols. Further, suitable detergents and ethoxylated alcohols permit an effective microemulsion and effective dispersion of the complex for application. In compositions where the active ingredient is a lipase associated with a fatty acid or derivative, polyoxyalkylene polymers are advantageously added in the form of the above-mentioned ethoxylated alcohols. This can be done in any composition of the invention. However, in those compositions where the moiety comprises a saccharide core esterified with fatty acids, polyoxyalkylene polymers may be derivatized directly to the core. In any case, a preferred form of polyoxyalkylene is polyoxyethylene.

Regardless of the nature of the active ingredient used, addition of surfactants is required in order to complete the effective complex. It appears that the order of addition of surfactants is important. In the case of hydrophobic/hydrophilic moieties where a polyoxyalkylene is already included, further addition of such polymers may be unnecessary. However, in the case of embodiments where the hydrophobic/hydrophilic moiety is a complex with denatured lipase, it is often necessary or desirable to include a source of such polyoxyalkylene polymers. Inclusion of additional such polymers may also be desirable even though the hydrophobic/hydrophilic moiety contains some level of such entities. In these cases, initially, an alkoxylated, typically ethoxylated, linear alcohol or alkoxylated/ethoxylated mixture of alcohols containing 9-11 carbons is added followed by homogenizing. This is optionally followed by adding an ethoxylated linear alcohol of 11 carbons, and then homogenizing. This is then followed by adding a surfactant blend for microemulsion formation and homogenizing, and finally an anionic surfactant is added. The final composition is then homogenized. By using appropriate concentrations, the resultant forms a concentrated premix which then can be diluted for application to agricultural crops.

Thus, in the first step described above, mixtures of linear alcohols of suitable chain lengths with an appropriate degree of alkoxylation can be used. The proportions of $C_9$, $C_{10}$ and $C_{11}$ alcohols can be variable, but typically, the mixture contains at least 25 percent of $C_9$ linear alcohols. Commercially available mixtures are typically ethoxylated to varying degrees, 2.5 moles of ethoxylation in the polymeric chain being preferred. Although ethoxylation is the most typical commercially available form, there is no theoretical reason that methoxylation or formation of polymeric ethers with higher chain alcohols could not be used. Tomah Reserve, Inc. markets a series of linear alcohols trademarked Tomadol™. The Tomadol™ compositions vary in chain length of the alcohol and number of moles of ethoxylation. For compositions where the alcohol contained 11 carbons, 7 moles of ethoxylation per mole of alcohol appeared optimal; 9 moles resulted in a solid at room temperature. Further, in compositions which contain mixtures of 9-11 carbon alcohols, 2.5 moles ethoxylation per mole of alcohol appeared to exhibit the best insect cuticle penetration.

Similarly, in the second (optional) step, $C_{11}$ linear alcohols in ethoxylated form are also added. Typical levels of ethoxylation include 7 moles of monomer in the polymeric chain; as was the case with the ethoxylated mixture in the first step, other alkoxylated forms could be substituted.

In the third step, a surfactant blend for microemulsion formation is employed. Various commercial preparations are available, including those from Stepan Chemical Company, Winder, Georgia. Of seven microemulsion formulations produced by Stepan Chemical, the highly preferred formulation is commercially designated H306A. The company will produce this formulation on special order of 20,000 lb. batches.

Microemulsion concentrate formulations such as are described by Skelton, P. R., "Pesticide Microemulsion Concentrate Formulations Utilizing Fatty Acid Methyl Esters as Solvent Alternatives," *Pesticide Formulations and Application Systems*: 13th Vol., ASTM STP 1183, Paul D. Berger, Bala N. Devisetty, and Franlin R. Hall, Eds, American Society for Testing and Materials, Philadelphia, 1993. Components can include combinations of the following: methyl esters, sorbitan ester ethoxylates, butoxy block copolymer, alkyl benzene sulfonic acid, and calcium salt. Alternatives for the ethoxylate and/or the block copolymer can be castor oil ethyoxylates. The foregoing are only examples, and the formulations are not limited to those components. Other microemulsion formulations are available.

In the fourth step, an anionic detergent or mixture of anionic detergents is used. Anionic surfactants, such as sodium lauryl sulfate and ammonium lauryl sulfate are known. In general, such surfactants include: alkylarylsulfonates, linear alkylbenzene sulfonates, alkane sulfonates, alcohol sulfates, alcohol ether sulfates, polyether carboxylates, olefin sulfonates, a-sulfomonocarboxylic esters, sulfosuccinates, phosphorus-containing anionics, and phosphate esters. Commercial mixtures are also available, although the variety of options available has decreased due to the introduction of siloxane-based surfactants now more commonly used in agriculture. However, anionic detergents are important in the compositions of the invention for several reasons. First, the anionic surfactant is believed to attach to the remainder of the lipase with which the oil, such as triolein, is associated. Anionic surfactants would associate, also, with the hydrophilic core in the case of sugar-based moieties. The result is that the complex, bearing a negative charge, will be more effective in binding nematode membranes in the soil. Second, in the case of acidic soils, additional anionic surfactant is desirable to neutralize the positive charges in the environment. One anionic surfactant currently marketed is Atsurf 1910 which, in its newer version at surf 1910 HF with a higher flash point, is less desirable that the version previously sold.

Typically, the composition is diluted 1:200, 1:500, 1:1000, or 1:2000 for application. The final concentration of the fatty acid backbone component is on the order of 200 ppm. The diluted composition must be clear and not turbid. Initially, is apparent that any dilution which does not appear clear to the naked eye should be rejected. It is preferable, however, that the turbidity of the final composition be less than 3 NTU, more preferably less than 2.5 NTU, and most preferably less than 1.0 NTU as measured in a turbidometer. The dilution may result in a satisfactorily clear solution without further agitation, or it may be necessary to stir, shake or vortex or otherwise agitate the dissolved components in order to effect clarity. Application of the solution can be by conventional means such as irrigation, spraying, and the like. Suitable target crops are any that are affected by undesired infestation by bacteria, fingi or nematodes, in particular by nematodes. The composition has been extensively tested on pineapple.

In somewhat more detail, the premix is diluted with additional surfactant and emulsifier, if desired, to the requisite dilution. The dilution is determined by the extent of infestation, the nature of the crop, and its stage of development. After dilution to form an additional clear microemulsion as described above, the diluted material is applied to the surface of the plots containing the plants. If desired, observations of the effectiveness of the pesticide may be taken systematically. Such observations may include the health of the plant generally, or may also involve specific measurement of pest viability. As exemplified below, suitable dilutions were able to lower nematode viability on pineapple crops to a very low level.

Soil moisture levels are important. If the soil is water saturated, the solution will not penetrate the soil particles and effectiveness drops. Thus, if it rains and the soil becomes soggy, it is preferred to delay application. Similarly, if a large amount of water is added as a post wet treatment, the effects may be diluted. Rains after application may also affect effectiveness. Larger or more concentrated dosages will kill within 1 day, some of the stronger formulations will kill 100% in 45 minutes of exposure. Weaker formulations may take several days to reach the same effectiveness.

The particular choice of formulation and the level of dilution may also determine the level and type of possible side effects on plant growth and health. In some formulations on some plants, growth is enhanced in addition to effecting nematode control. In some cases, the formulations may be slightly inhibitory or toxic. In general, the preparations which include fungal digested oil in relatively high concentrations are best used on pineapples as target crops and work less effectively, when taken in terms of total effect, on tomatoes. However, these aspects are independent of the nematode control aspects of the formulation and the formulations and dilution levels can readily be optimized for any particular type of plant.

The more general carrier formulations of the invention are designed to assist dispersal and penetration of active ingredients such as pesticides or drugs. However, in some instances, the invention compositions may themselves have applicability as pesticides where membrane disruption is the only requirement for effectiveness. Further, the compositions with or without active ingredients may be used as formulated, or, especially with respect to application to crops, may be diluted in water, often to a vary high degree—i.e., dilutions of 1:10, 1:100, 1:1,000 or 1:10,000 may be acceptable depending on the context. In all cases, for maximum effectiveness, the final formulation should appear clear to the naked eye. If the turbidity is measured with instrumentation, it is preferred that the turbidity be less than 5 NTU, more preferably less than 3 NTU, and most preferably less than 1 NTU.

The composition'three essential components can further be described as follows:

The first component is a linear alcohol containing 7-12C, preferably 9-11C which is derivatized with a polyalkoxylene moiety, such as polyethylene oxide. Of course, mixtures of such linear alcohols can be used. The variables in this component include the number of carbons in the linear alcohol and the number and nature of alkoxylene units in the polyalkoxylation. Generally, mixtures containing approximately equal amounts of alcohols containing 9-11 carbons is preferred, although a preponderance of $C_{11}$ alcohols, especially where the polyalkoxylene ratio is relatively high—i.e., on the order of 5-9, may be included within this mixture or added subsequently. It is not necessary to include a mixture of such alcohols and a single, for example, $C_{10}$ alcohol could be used. The degree of polyethoxylation or polyalkoxylation is also acceptable within a range; in general, the majority of the alcohols should be polyalkoxylated in a ratio of 2-6 alkoxylene units is preferred. For practical reasons, polyethoxylene is the preferred polyalkoxylene—thus it is possible, in a preferred embodiment, to consider the linear alcohols "PEGylated."

The degree of polyalkoxylation that is optimum for a particular composition will depend on the nature of the alkoxylene in the polymer, the chain length of the linear alcohol, and the nature of the remaining polyalkoxylated alcohols in any mixture that might be used. In a typical formulation, a mixture of $C_9$-$C_{11}$ linear alcohols at a PEGylation ratio of 2.5 moles of ethylene glycol per linear alcohol is used, supplemented with a $C_{10}$ or $C_{11}$ PEGylated alcohol at a ratio of 6-8, preferably 7 moles of ethylene glycol per linear alcohol unit.

The alkoxylation ratio describes the ratio of alkoxylene units to linear alcohol. The ratio may represent an average—i.e., not all of the molecules in the mixture may show the same ratio.

Polyalkoxylated alcohols suitable for inclusion in the compositions of the invention may be formulated independently or are commercially available. For example, Tomah Reserve, Inc. markets such mixtures.

The second required component is a surfactant or mixture of surfactants which promotes microemulsion formation. Typically, the surfactants included in this component are nonionic and amphiphilic. Microemulsion formation is apparently best promoted by mixtures of such surfactants. Suitable components of such mixtures include such nonionic surfactants as esterified phospholipids and sorbitol esters with long chain fatty acids. Suitable mixtures can be formulated independently and are also commercially available, for example, from the Stepan Chemical Co., Winder, Ga.

The third component is an anionic detergent, such as the ammonium and metal salts of sulfonated fatty acids. Suitable anionic detergents include, for example, ammonium and sodium lauryl sulfate, aromatic sulfonic acid salts, and the like.

Optimum results in terms of encouraging dispersal and penetration are obtained when the components of the mixture are added in the order listed above with mixing after each step. Thus, the microemulsion-enhancing surfactant is added to the polyalkoxylated linear alcohol component(s) and thoroughly blended prior to the addition of the anionic detergent. In all cases, suitable agitation and mixing are required. The ratios of the components can vary, but it is preferred to include about 1-5 parts polyalkoxylated linear alcohol to about 9-15 parts microemulsion enhancer to about 9-15 parts anionic detergent. Particularly preferred ratios of components comprise about 5-7 parts polyalkoxylated alcohols to 11-13 parts microemulsion enhancer to about 11-13 parts anionic detergent. A particularly preferred ratio is 7:12:12.

The final form of formulation which includes the compositions of the invention depends on the nature of the application. For pharmaceutical applications and topical drug delivery, preferably the composition containing an active ingredient is applied in undiluted form. The active ingredient or active ingredients can be added directly to the composition or, alternatively, the composition can be built around the active ingredients. Any pharmaceutically active compound is an appropriate active ingredient, including small molecule pharmaceuticals, proteins, antiviral agents, antibiotics, anti-inflammatory agents, beta blockers, and the like. The reader is referred, for example, to the current edition of the Physician'Desk Reference, incorporated herein by reference.

For a pharmaceutical use, additional components may be added to the final formulation so long as they do not distort the dispersant/penetrant qualities of the carrier composition of the invention. For example, antioxidants, stabilizers, and salts for controlling pH may be added to the formulation. Small amounts of diluent may also be included.

For agricultural applications, although the compositions may be used per se as, for example, nematocides by virtue of their ability to disrupt membranes, typically, they are supplied with an additional active ingredient such as an herbicide, pesticide or nutrient. Because of the requirement to provide the active ingredient over a wide area, the final formulation is typically diluted. Quite large dilution ratios are frequently employed so that the active ingredient is present only in 100-500 ppm, for example. Typical active ingredients include cytokinins, auxins, gibberellic esters, indole acetic acid, and similar compounds. Preferred compounds include zeatin, gibberellic acid, and abscisic acid. Also included are pesticides including synthetic and biological-based pesticides and, in appropriate cases, herbicides.

In all cases, the final formulation should be clear to the naked eye. Preferably, the final formulation has a turbidity of less than 5 NTU, and more preferably less than 1 NTU.

In one preferred preparation, initially, an alkoxylated, typically ethoxylated, linear alcohol or alkoxylated/ethoxylated mixture of alcohols containing 9-11 carbons is added to one or more active ingredients followed by homogenizing. This is optionally followed by adding an ethoxylated linear alcohol of 11 carbons, and then homogenizing. This is then followed by adding a surfactant blend for microemulsion formation and homogenizing, and finally an anionic surfactant is added. The final composition is then homogenized. By using appropriate concentrations, the resultant forms a concentrated premix which then can be diluted for application to agricultural crops, or, if the active ingredient is a drug, may be used in undiluted form.

Thus, in the first step described above, mixtures of linear alcohols of suitable chain lengths with an appropriate degree of alkoxylation can be used. The proportions of $C_9$, $C_{10}$ and $C_{11}$ alcohols can be variable, but typically, the mixture contains at least 25 percent of $C_9$ linear alcohols. Commercially available mixtures are typically ethoxylated to varying degrees, 2.5 moles of ethoxylation in the polymeric chain being preferred. Although ethoxylation is the most typical commercially available form, there is no theoretical reason that methoxylation or formation of polymeric ethers with higher chain alcohols could not be used. Tomah Reserve, Inc. markets a series of linear alcohols trademarked Tomadol™. The Tomadol™ compositions vary in chain length of the alcohol and number of moles of ethoxylation. For compositions where the alcohol contains 11 carbons, 7 moles of ethoxylation per mole of alcohol appears optimal; 9 moles can result in a solid at room temperature. Further, in compositions which contain mixtures of 9-11 carbon alcohols, 2.5 moles ethoxylation per mole of alcohol appears to exhibit the best insect cuticle penetration.

In the second optional step, $C_{11}$ linear alcohols in ethoxylated form are also available. Typical levels of ethoxylation include 7 moles of monomer in the polymeric chain; as was the case with the ethoxylated mixture in the first step, other alkoxylated forms could be substituted.

In the third step, a surfactant blend for microemulsion formation is employed. Various commercial preparations are available, including those from Stepan Chemical Company, Winder, Ga. Of seven microemulsion formulations produced by Stepan Chemical, the highly preferred formulation is commercially designated H306A. The company will produce this formulation on special order of 20,000 lb. batches.

In the fourth step, an anionic detergent or mixture of anionic detergents is used. Anionic surfactants, such as sodium lauryl sulfate and ammonium lauryl sulfate are known. Commercial mixtures are also available, although the variety of options available has decreased due to the introduction of siloxane-based surfactants now more commonly used in agriculture. However, anionic detergents are required in the compositions of the invention. One anionic surfactant currently marketed is Atsurf 1910 which, in its newer version Atsurf 1910 HF with a higher flash point, is less desirable that the version previously sold.

For agricultural uses, the composition is diluted 1:200, 1:500, 1:1000, or 1:2000 for application. The final concentration of the active ingredient is on the order of 200 ppm. The diluted composition must be clear and not turbid. Any dilution which does not appear clear to the naked eye should be rejected. It is preferable, however, that the turbidity of the final composition be less than 3 NTU, more preferably less than 2.5 NTU, and most preferably less than 1.0 NTU as measured in a turbidometer. The dilution may result in a satisfactorily clear solution without further agitation, or it may be necessary to stir, shake or vortex or otherwise agitate the dissolved components in order to affect clarity.

The following examples are intended to illustrate but not to limit the invention.

EXAMPLE 1

Preparation of Test Microemulsions

Four varying preparations of the pesticidal microemulsion were prepared as shown in Table 1 below. The preparation procedure was as follows: Treated and lipase associated sunflower oil was prepared by mixing 200 ml of a solution containing 200 mg of Validase 8000 (Valley Research Technologies, South Bend, Ind.) with 200 ml of Optimum™ sunflower oil, Optimum Quality Grains, Inc., Urbandale, Iowa. The resultant mixture was homogenized and incubated for 24 hours at 40° C. The mixture was then treated for 10 minutes at 95° C. effecting a separation into an aqueous and lipid phase. The lipid phase was recovered.

A few large particles were formed which were removed by filtration through Whatman No. 1 filter paper. This mixture could be stored for as long as two years.

Final formulation of the concentrated pesticide required the addition of surfactants. The surfactants were added in the order described below; the ratio of the surfactants to the digested sunflower oil in various formulations is shown in Table 1. The order of addition is important.

To the treated sunflower oil was first added Tomadol 91-2.5, a Tomah Reserve Inc. product. This is a linear alcohol, ethoxylated $C_9$-$C_{11}$ with 2.5 moles of ethoxylation. After the addition, homogenization was performed by stirring at 15,000 rpm maintaining the temperature at room temperature. This was followed by addition of Tomadol 1-7, another Tomah Reserve product which comprises linear alcohols of $C_{11}$ ethoxylated with 7 moles ethoxylation. The resulting mixture was again homogenized by stirring at 15,000 rpm. This was followed by addition of H306A, a product for microemulsion formation produced by the Stepan Chemical Company (Winder, Ga.). The composition is proprietary, but is commercially available. Following the addition of H306A, homogenization was performed again by stirring at 15,000 rpm. This was followed by addition of Atsurf 1910, a product of Uniqema (Wilmington, Del.) which is a commercially available proprietary blend of anionic surfactants. The mixture was homogenized by stirring at 15,000 rpm. The final premix formulation was clear or cloudy as shown in Table 1 depending on the ratios of digested oils to surfactants.

The premix was diluted with water in a ratio to obtain at 200 ppm of the treated oil in the dilution and tested for ability to kill reniform nematodes in 30 inch×2 inch soil tubes. The percentages killed are given in Table 1. Also shown in Table 1 are the percentage kills of reniform nematodes when the premix was tested in water rather than soil at 200 ppm of the treated sunflower oil, with surfactants.

TABLE 1

| Components | 081499-3 | 081499-2 | 081599-1 | 081599-2 |
|---|---|---|---|---|
| Treated Sunflower Oil | 5 | 4 | 4 | 4 |
| H306 | 12 | 12 | 12 | 12 |
| 1910 | 12 | 12 | 12 | 12 |
| 91-2.5 | 5 | 4 | 5 | 6 |
| 1-7 | 2 | 2 | 2 | 2 |
| % DSO | 13.9 | 11.8 | 11.4 | 11.1 |
| Ratio DSO/Surfactant | 1:6.2 | 1:7.5 | 1:7.75 | 1:8 |
| Emulsion | CLOUDY | Clear | Clear | Clear |
| Water Test at 200 ppm % RENIFORM KILL | — | 97% | 98.5% | 96.5% |
| SOIL TUBE TEST at 200 ppm digested oil | — | 53% | 100% | 75% |

As shown in Table 1, although all of the clear preparations were effective, preparation 081599-1 was the most effective in the soil tests.

EXAMPLE 2

Additional Formulations

Table 2 shows additional formulations of nematicidal materials.

For formulation 0510099-5, the hydrophobic/hydrophilic component is Dupont sunflower oil which has been treated with *Laetiporus* culture filtrate for 24 hours.

In formulation 122699-7, the hydrophobic/hydrophilic ingredient is Dupont sunflower oil which has been treated with Validase for 24 hours.

In formulation 122699-6, the hydrophobic/hydrophilic ingredient is the sugar alcohol ester Toximul SEE-340 which has been predissolved in aromatic 100.

In formulation 011500-1, the hydrophobic/hydrophilic component is safflower oil which is treated with a nine-months fermented Laetiporus culture.

TABLE 2

|  | 051099-5 | 122699-7 | 122699-6 | 011500-1 |
|---|---|---|---|---|
| Hydrophobic/Hydrophilic Treated Oil or Sugar Ester | 3 | 3 | 3 | 3 |
| H306A | 12 | 14 | 20 | 12 |
| 1910 | 12 | 12 | 12 | 12 |
| 91-2.5 | 4 | 4 | 4 | 4 |
| 1-7 | 2 | 2 | 2 | 2 |
| Aromatic 100 | — | — | 6 | — |
| % Oil or SEE-340 | 9.09 | 8.57 | 6.4 | 9.09 |
| NTU 200 ppm | 0.7 | 1.2 | 2.2 |  |
| NTU 24 hrs later 200 ppm | 0.7 | 1.2 | 1 |  |
| NTU 400 ppm |  |  | 2.4 | 0.9 |
| NTU 200 ppm |  |  | 2.3 |  |
| Ratio ai/surfactant | 1 to 10 | 1 to 10.7 | 1 to 14.7 | 1 to 10 |
| 500 ppm ai | 5.5 ml/l | 5.75 ml/l | 7.83 ml/l | 5.5 ml/l |
| 400 ppm ai | 4.4 ml/l | 4.6 ml/l | 6.26 ml/l | 4.4 ml/l |
| 200 ppm ai | 2.2 ml/l | 2.3 ml/l | 3.13 ml/l | 2.2 ml/l |
| 100 ppm ai | 1.1 ml/l | 1.15 ml/l | 1.57 ml/l | 1.1 ml/l | ai = active ingredients

The formulation 12269-6 can also be represented as follows where the commercial sources of the components are noted.

All Surfactant Nematicide Formulation 122699-6

|  |  |  | ml |
|---|---|---|---|
| Stepan Company | Sorbitan trioleate | Toximul SEE-340 | 60 |
| Stepan Company | Microemulsion blend | H306A | 400 |
| Unqema | Anionic surfactant | Atsurf 1910 | 240 |
| Tomah Reserve | Linear Alcohol | 91-2.5 | 80 |
| Tomah Reserve | Linear Alcohol | 1-7.0 | 40 |
| Exxon Chemical Co. | Agriculture solvent | Aromatic 100 | 120 |
|  |  | Total ml | 940 |
|  |  | 500 ppm 2.0 NTU |  |
|  |  | 250 ppm 1.5 NTU |  |

In the foregoing formulations it has been shown that in the formulation treated with *Laetiporus fungi*, no hydrolyses of oleic acid esters appears to have occurred. In contrast, in those formulations where the oil is treated with Validase, some hydrolysis appears to take place. While NTU for formulation 051099-5 and 122699-7 at 200 ppm was stable over 24 hours, NTU for 122699-6 at 200 ppm decreased over this time period.

The formulations prepared were subjected to soil tube testing which involves the dripping of a test solution from a separatory funnel on to an upright 2 inch diameter plastic pipe, 30 inches long. The pipe is cut at 18 inches from the top. This would represent 18 inches of soil depth as in the first section. The second section consists of 12 inches of soil. The bottom section has a bottom screen cover to prevent the soil from falling out. As soil is filled into the pipe sections, soil samples are placed on the side for the control nematode populations. Nematode populations are determined in the soil batch before soil testing commences. The two sections are joined by a rubber gasket secured by adjustable gasket clamps. The test solution is dripped into the top of the soil tube and the solution percolates through the soil tube and drips out. When the solution stops percolation, the soil tubes are disassembled and the soil is placed in a plastic bag for storage. Depending on the conditions, 1 to 7 days may elapse before the soil nematodes are extracted via the Baermann Funnel system. Each soil tube will have 2 controls and 2 treatments, a set of control and treatment for each section of the soil tube.

Some formulations to be tested may only show effectiveness in the top 18 inches, some may show no effectiveness in soil and some may show effectiveness throughout the 30 inch soil tube.

If a formulation shows effectiveness in the soil tube testing, the formulation will show effectiveness in pots and field tests as well.

The results of testing these formulations of Table 2 are shown in Tables 3-7.

TABLE 3

SOIL TUBE DATA 051099-5

NEMATODE COUNTS PER 50 ML OF SOIL

| Date | Formula | ppm active ingredient | Replicate | Soil Tube Section | | Total | Reniform | Spiral | Rootknot | Others |
|---|---|---|---|---|---|---|---|---|---|---|
| Jan. 12, 2000 | 051099-5 | 125 | 1 | 510 | 1-Control | 480 | 50 | 90 | 100 | 240 |
|  |  |  |  |  | 2-Control | 460 | 60 | 100 | 150 | 150 |
|  |  |  |  |  | 3-Treated | 70 | 0 | 20 | 30 | 20 |
|  |  |  |  |  | 4-Treated | 310 | 10 | 30 | 100 | 170 |
| Jan. 12, 2000 | 051099-5 | 125 | 2 | 511 | 1-Control | 450 | 50 | 100 | 110 | 190 |
|  |  |  |  |  | 2-Control | 560 | 60 | 100 | 190 | 210 |
|  |  |  |  |  | 3-Treated | 50 | 0 | 10 | 10 | 30 |
|  |  |  |  |  | 4-Treated | 420 | 20 | 30 | 50 | 320 |
| Jan. 12, 2000 | 051099-5 | 125 | 3 | 512 | 1-Control | 1180 | 80 | 250 | 300 | 550 |
|  |  |  |  |  | 2-Control | 1240 | 90 | 260 | 280 | 610 |
|  |  |  |  |  | 3-Treated | 40 | 0 | 10 | 10 | 20 |
|  |  |  |  |  | 4-Treated | 370 | 30 | 50 | 90 | 200 |

Section 1 and 3 are the control and treatment of the first 18 inches of soil
Section 2 and 4 are the control and treatment of the next 12 inches of soil
Formulations were dripped into the soil tube, approximately 1 liter in 2 hours

TABLE 4

SOIL TUBE DATA 122699-7

NEMATODE COUNTS PER 50 ML OF SOIL

| Date | Formula | ppm active ingredient | Replicate | Soil Tube Section | | Total | Reniform | Spiral | Rootknot | Others |
|---|---|---|---|---|---|---|---|---|---|---|
| Jan. 12, 2000 | 122699-7 | 400 | 1 | 504 | 1-Control | 1350 | 120 | 310 | 400 | 520 |
|  |  |  |  |  | 2-Control | 2620 | 240 | 180 | 500 | 1700 |
|  |  |  |  |  | 3-Treated | 20 | 0 | 0 | 10 | 10 |
|  |  |  |  |  | 4-Treated | 360 | 20 | 50 | 200 | 90 |
| Jan. 12, 2000 | 122699-7 | 400 | 2 | 505 | 1-Control | 1140 | 120 | 170 | 190 | 660 |
|  |  |  |  |  | 2-Control | 1040 | 40 | 60 | 170 | 770 |
|  |  |  |  |  | 3-Treated | 0 | 0 | 0 | 0 | 0 |
|  |  |  |  |  | 4-Treated | 140 | 0 | 0 | 20 | 120 |

TABLE 4-continued

SOIL TUBE DATA 122699-7

| | | | | | | NEMATODE COUNTS PER 50 ML OF SOIL | | | | |
|---|---|---|---|---|---|---|---|---|---|---|
| Date | Formula | ppm active ingredient | Replicate | | Soil Tube Section | Total | Reniform | Spiral | Rootknot | Others |
| Jan. 12, 2000 | 122699-7 | 400 | 3 | 506 | 1-Control | 760 | 40 | 60 | 110 | 550 |
| | | | | | 2-Control | 640 | 40 | 50 | 120 | 430 |
| | | | | | 3-Treated | 20 | 0 | 0 | 10 | 10 |
| | | | | | 4-Treated | 50 | 0 | 0 | 30 | 20 |

Section 1 and 3 are the control and treatment of the first 18 inches of soil
Section 2 and 4 are the control and treatment of the next 12 inches of soil
Formulations were dripped into the soil tube, approximately 1 liter in 2 hours

TABLE 5

SOIL TUBE DATA 122699-9

| | | | | | | NEMATODE COUNTS PER 50 ML OF SOIL | | | | |
|---|---|---|---|---|---|---|---|---|---|---|
| Date | Formula | ppm active ingredient | Replicate | | Soil Tube Section | Total | Reniform | Spiral | Rootknot | Others |
| Jan. 12, 2000 | 122699-6 | 400 | 1 | 507 | 1-Control | 810 | 60 | 70 | 150 | 530 |
| | | | | | 2-Control | 1000 | 70 | 150 | 200 | 580 |
| | | | | | 3-Treated | 0 | 0 | 0 | 0 | 0 |
| | | | | | 4-Treated | 10 | 0 | 0 | 0 | 10 |
| Jan. 12, 2000 | 122699-6 | 400 | 2 | 508 | 1-Control | 1240 | 70 | 120 | 130 | 920 |
| | | | | | 2-Control | 1260 | 80 | 140 | 170 | 870 |
| | | | | | 3-Treated | 0 | 0 | 0 | 0 | 0 |
| | | | | | 4-Treated | 50 | 0 | 0 | 20 | 30 |
| Jan. 12, 2000 | 122699-6 | 400 | 3 | 509 | 1-Control | 610 | 40 | 70 | 150 | 350 |
| | | | | | 2-Control | 590 | 30 | 50 | 100 | 410 |
| | | | | | 3-Treated | 10 | 0 | 0 | 0 | 10 |
| | | | | | 4-Treated | 10 | 0 | 0 | 10 | 0 |

Section 1 and 3 are the control and treatment of the first 18 inches of soil
Section 2 and 4 are the control and treatment of the next 12 inches of soil
Formulations were dripped into the soil tube, approximately 1 liter in 2 hours

TABLE 6

SOIL TUBE DATA 122699-6

| | | | | | | NEMATODE COUNTS PER 50 ML OF SOIL | | | | |
|---|---|---|---|---|---|---|---|---|---|---|
| Date | Formula | ppm active ingredient | Replicate | | Soil Tube Section | Total | Reniform | Spiral | Rootknot | Others |
| Jan. 13, 2000 | 122699-6 | 125 | 1 | 528 | 1-Control | 950 | 50 | 60 | 100 | 740 |
| | | | | | 2-Control | 1100 | 100 | 150 | 250 | 600 |
| | | | | | 3-Treated | 50 | 10 | 10 | 20 | 10 |
| | | | | | 4-Treated | 150 | 20 | 20 | 30 | 80 |
| Jan. 13, 2000 | 122699-6 | 125 | 2 | 529 | 1-Control | 1200 | 130 | 180 | 220 | 670 |
| | | | | | 2-Control | 1800 | 150 | 250 | 300 | 1100 |
| | | | | | 3-Treated | 50 | 10 | 10 | 10 | 20 |
| | | | | | 4-Treated | 70 | 10 | 10 | 20 | 30 |
| Jan. 13, 2000 | 122699-6 | 125 | 3 | 530 | 1-Control | 1200 | 90 | 200 | 300 | 610 |
| | | | | | 2-Control | 1100 | 110 | 180 | 250 | 560 |
| | | | | | 3-Treated | 50 | 0 | 0 | 20 | 30 |
| | | | | | 4-Treated | 220 | 20 | 40 | 60 | 100 |

Section 1 and 3 are the control and treatment of the first 18 inches of soil
Section 2 and 4 are the control and treatment of the next 12 inches of soil
Formulations were dripped into the soil tube, approximately 2 liters in 4 hours

TABLE 7

SOIL TUBE DATA 011500-1

| Date | Formula | ppm active ingredient | Replicate | Soil Tube | Section | Total | Reniform | Spiral | Rootknot | Others |
|---|---|---|---|---|---|---|---|---|---|---|
| | | | | | | NEMATODE COUNTS PER 50 ML OF SOIL | | | | |
| Jan. 17, 2000 | 011500-1 | 500 | 1 | 531 | 1-Control | 1120 | 120 | 250 | 280 | 470 |
| | | | | | 2-Control | 520 | 60 | 100 | 150 | 210 |
| | | | | | 3-Treated | 20 | 0 | 10 | 10 | 0 |
| | | | | | 4-Treated | 150 | 0 | 20 | 50 | 80 |
| Jan. 17, 2000 | 011500-1 | 500 | 2 | 532 | 1-Control | 1500 | 100 | 250 | 350 | 800 |
| | | | | | 2-Control | 1100 | 90 | 150 | 250 | 610 |
| | | | | | 3-Treated | 20 | 0 | 0 | 0 | 20 |
| | | | | | 4-Treated | 30 | 0 | 10 | 10 | 10 |
| Jan. 17, 2000 | 011500-1 | 500 | 3 | 533 | 1-Control | 1500 | 100 | 250 | 450 | 700 |
| | | | | | 2-Control | 1120 | 110 | 260 | 350 | 400 |
| | | | | | 3-Treated | 0 | 0 | 0 | 0 | 0 |
| | | | | | 4-Treated | 70 | 0 | 20 | 30 | 20 |

Section 1 and 3 are the control and treatment of the first 18 inches of soil
Section 2 and 4 are the control and treatment of the next 12 inches of soil
Formulations were dripped into the soil tube, approximately 1 liter in 2 hours As shown in these tables, all of the formulations were effective as compared to controls. The counts of various namatodes are consistently smaller in both areas of the tubes than for controls. Formulation 122699-6 at 400 parts per million is particularly effective.

As this formulation is particularly successful, alternative representations of the data obtained with this formulation in the soil tube tests at 125 and 400 parts per million of active ingredient, respectively, are presented in Tables 8 and 9. The active ingredient is sorbitan trioleate and the ppm ai represents parts per million of this component.

TABLE 9

SOIL TUBE DATA 122699-6

| Date | Formula | ppm ai | Replicate | Soil Tube | Section | Total | Reniform | Spiral | Rootknot | Others |
|---|---|---|---|---|---|---|---|---|---|---|
| | | | | | | Percentage Reduction in Nematode Count | | | | |
| Jan. 13, 2000 | 122699-6 | 125 | 1 | 528 | 1 | 95% | 80% | 83% | 80% | 99% |
| | | | | | 2 | 86% | 80% | 87% | 88% | 87% |
| Jan. 13, 2000 | 122699-6 | 125 | 2 | 529 | 1 | 96% | 92% | 94% | 95% | 97% |
| | | | | | 2 | 96% | 93% | 96% | 93% | 97% |
| Jan. 13, 2000 | 122699-6 | 125 | 3 | 530 | 1 | 96% | 100% | 100% | 93% | 95% |
| | | | | | 2 | 80% | 82% | 78% | 76% | 82% |
| | | | Average Percentage | | 1 | 95.7% | 90.7% | 92.3% | 89.3% | 97% |
| | | | Average Percentage | | 2 | 87.3% | 85% | 87% | 85.7% | 88.7% |

Section 1 is the first 18 inches of soil in the soil tube 2 inch diameter, 30 inches long
Section 2 is the lower 12 inches of the soil tube
Formulations were dripped into the soil tube at a rate of 2 liters in 4 hours

TABLE 10

SOIL TUBE DATA 122699-6

| Date | Formula | ppm ai | Replicate | Soil Tube | Section | Total | Reniform | Spiral | Rootknot | Others |
|---|---|---|---|---|---|---|---|---|---|---|
| | | | | | | Nematode Counts Per 50 Ml Of Soil | | | | |
| Dec. 27, 1999 | 122699-6 | 400 | 1 | 507 | 1-Control | 810 | 60 | 70 | 150 | 530 |
| | | | | | 2-Control | 1000 | 70 | 150 | 200 | 580 |
| | | | | | 3-Treated | 0 | 0 | 0 | 0 | 0 |
| | | | | | 4-Treated | 10 | 0 | 0 | 0 | 10 |
| Dec. 27, 1999 | 122699-6 | 400 | 2 | 508 | 1-Control | 1240 | 70 | 120 | 130 | 920 |
| | | | | | 2-Control | 1260 | 80 | 140 | 170 | 870 |
| | | | | | 3-Treated | 0 | 0 | 0 | 0 | 0 |
| | | | | | 4-Treated | 50 | 0 | 0 | 20 | 30 |

TABLE 10-continued

SOIL TUBE DATA 122699-6

| Date | Formula | ppm ai | Repli-cate | Soil Tube | Section | Nematode Counts Per 50 Ml Of Soil | | | | |
|---|---|---|---|---|---|---|---|---|---|---|
| | | | | | | Total | Reniform | Spiral | Rootknot | Others |
| Dec. 27, 1999 | 122699-6 | 400 | 3 | 509 | 1-Control | 610 | 40 | 70 | 150 | 350 |
| | | | | | 2-Control | 590 | 30 | 50 | 100 | 410 |
| | | | | | 3-Treated | 10 | 0 | 0 | 0 | 10 |
| | | | | | 4-Treated | 10 | 0 | 0 | 10 | 0 |

Section 1 and 3 are the control and treatment of the first 18 inches of soil in a 2 in pipe, 30 inches long
Section 2 and 4 are the control and treatment of the next 12 inches of soil in a 2 in pipe, 30 inches long
Formulations were dripped into the soil tube, approximately 1 liter in 2 hours

EXAMPLE 3

Results of Field Tests

A field test evaluated the following formulations. The experimental design was as follows:

Randomized complete block 14 treatments×5 replications (2 plant per replication)

Treatrments

| | Treatments: |
|---|---|
| AX | Control- water only |
| A0 | Surfactant/Emulsifier A- no ABR |
| AC | Surfactant/Emulsifier A- Safflower Oil @ 500 ppm |
| A500 | Surfactant/Emulsifier A(formulation 42399-1)- ABR @ 500 ppm |
| A2000 | Surfactant/Emulsifier A(formulation 42399-1)- ABR @ 2000 ppm |
| BX | Control- water only |
| B0 | Surfactant/Emulsifier B - no ABR |
| BC | Surfactant/Emulsifier B- Sunflower Oil @ 500 ppm |
| B500 | Surfactant/Emulsifier B(formulation 051099-5)- ABR @ 500 ppm |
| B2000 | Surfactant/Emulsifier B(formulation 051099-5)- ABR @ 2000 ppm |
| C0 | Surfactant/Emulsifier D(formulation 052299-1)- ABR @ 2000 ppm |
| CC | Surfactant/Emulsifier C- Safflower Oil @ 500 ppm |
| C500 | Surfactant/Emulsifier C(formulation 051799-1)- ABR @ 500 ppm |
| C2000 | Surfactant/Emulsifier C(formulation 051799-1)- ABR @ 2000 ppm |

As shown in the foregoing list, Surfactant/Emulsifier A, B, C, or D are based on the noted formulations. The noted formulations are composed of components listed as follows:

TABLE 8

| Treatment A series 042399-1 | Parts |
|---|---|
| *Laetiporus* treated Safflower Oil, 24 hour | 2 |
| ICI's Atsurf 1910 | 5 (proprietary anionic surfactants) |
| ICI's Atplus 401 | 1 (proprietary surfactants) |
| OSI Specialties' SilWet L7280 heptamethyl | 2 (polyalkyleneoxide modified Trisiloxane) |
| Loveland Industries' Blend | 1 (proprietary blend of surfactants) |
| Aldrich's Tween 85 | 1 (sorbitan esters) |

70 NTU at 200 ppm active ingredient

| Treatment B 051099-5 | Parts |
|---|---|
| *Laetiporus* treated Optimum Sunflower Oil, 24 hours | 3 |
| H306A | 12 |
| 1910 | 12 |
| 91-2.5 | 4 |
| 1-7.0 | 2 |

0.7 NTU at 200 ppm active ingredient

| Treatment CO 052299-1 | Parts |
|---|---|
| *Laetiporus* treated Optimum Sunflower Oil, 24 hours | 3 |
| H307AB Stepan Microemulsion Blend | 12 (Discontinued formulation from Stepan) |
| 1910 | 12 |
| 91-2.5 | 4 |
| 1-7.0 | 2 |

0.7 NTU at 200 ppm active ingredient

| Treatment C500 and C2000 051799-1 | Parts |
|---|---|
| *Laetiporus* treated optimum Sunflower Oil, 24 hours | 3 |
| H306 | 12 |
| 1910 | 12 |
| 91-2.5 | 4 |
| 1-7.0 | 2 |

1.1 NTU at 200 ppm active ingredient

Where—"ABR" is indicated, the hydrophobic/hydrophilic component is present. The notation "no ABR" indicates that this ingredient is absent as is any oil component whatsoever. Thus, for example, treatment A2000 represents formulation of 42399-1 as shown in Table 8, but diluted to 2000 parts per million with water. A500 indicates the same formulation, but diluted to 500 parts per million. AC represents the components of formulation 042399-1 without the Laetiporus treated safflower oil, but having substituted, in place of it, safflower oil without being treated. A0, which contains surfactants/emulsifier A—no ABR, contains all the components of the formulation shown except the treated safflower oil and no additional safflower oil is included. The remaining entries are interpreted in an analogous manner.

| LAYOUT Treatment Plots: 10 plants/treatment | | | | | |
|---|---|---|---|---|---|
| REP5 | REP4 | REP3 | REP2 | REP1 | ROAD |
| AX 5 | AX 4 | AX 3 | AX 2 | AX 1 | 1 |
| AO 5 | AO 4 | AO 3 | AO 2 | AO 1 | 2 |
| AC 5 | AC 4 | AC 3 | AC 2 | AC 1 | 3 |
| A500 5 | A500 4 | A500 3 | A500 2 | A500 1 | 4 |
| A2000 5 | A2000 4 | A2000 3 | A2000 2 | A2000 1 | 5 |
| C500 5 | B500 4 | BC 3 | BO 2 | BX 1 | 6 |
| BX 5 | B2000 4 | B500 3 | BC 2 | BO 1 | 7 |
| CC 5 | CO 4 | B2000 3 | B500 2 | BC 1 | 8 |
| C2000 5 | CC 4 | CO 3 | B2000 2 | B500 1 | 9 |
| B500 5 | C500 4 | CC 3 | CO 2 | B2000 1 | 10 |
| BO 5 | C2000 4 | C500 3 | CC 2 | CO 1 | 11 |
| CO 5 | BX 4 | C2000 1 | C500 2 | CC 1 | 12 |
| BC 5 | BO 4 | BX 3 | C2000 2 | C500 1 | 13 |
| B2000 5 | BC 4 | BO 3 | BX 2 | C2000 1 | 14 |

Procedure

A first or second ratoon crop field that is not scheduled for another crop cycle and has a history of high nematode populations will be selected. Fourteen beds will be selected and walkways between the beds will be trimmed for approximately 25 feet. The first plant line in each bed will be used for testing with every other plant receiving the proper treatment. A soil sample for nematode will be taken pre application from the first, third, fifth, seventh, ninth, eleventh, thirteenth, fifteenth, seventeenth and nineteenth plant in each treatment plant line. The first and third plant sample will be composited and recorded as replication 1, the fifth and seventh will be composited and recorded as replication 2. Samples will be composited in the same order so as to have 5 replications per treatment. Observations of plant color and vigor will be recorded and pictures will be taken pre application. Treatments will be applied to the second, fourth, sixth, eighth, tenth, twelfth, fourteenth, sixteenth, eighteenth and twentieth plants in each treatment plant line. Treatments will be applied in 2 liters of water, by hand, at the base of each plant using 2-liter coke bottles that have been punctured. Two liters per plant is approximately the amount that each plant would receive during a plantation practice Nemacur application in a ½ acre-inch of water. At one month post application another soil sample for nematodes will be taken from the treated plants and observations of any changes in plant color and vigor (along with post application pictures) will be made. These soil samples will also be composited, with the sample from plants two and four recorded as replication 1, six and eight being replication 2 and so forth until 5 replications are collected.

Records to Collect

1. Map with location of test plot.
2. Records of dates and amounts of product and water applied.
3. Soil samples for nematodes pre application (un-treated plants).
4. Soil samples for nematodes 6 weeks post application (treated plants).
5. Phytotoxicity observations at 1,2 and 3 months after application.

Results

Chronological Data

AX, AO, AC, A500 and A2000 treatment applications took place on May 17, 1999. These applications were not randomized, with each treatment being applied to every even numbered plant (from 2 to 20) in the same plant line. The remainder of the treatments were applied on May 24, 1999 and were randomized. Pre application soil collection was conducted on May 13, 1999 and post application soil collection was conducted Jul. 12, 1999. Post application samples were split in half The Maui Pine Ag Research lab and the University of Hawaii nematology lab each ran a set of samples using the elutriator and Baermann funnel techniques. This report will focus on the percent of reduction of nematode populations (pre application number of nematodes- post application number of nematodes/100), as pure numbers of nematodes can be misleading due to variation in the pre application counts.

Elutriator Results

Both Maui Pine and U.H. elutriator testing showed the B2000 treated plants to have the highest average percent reduction of all treatments. The Maui Pine data showed this percent reduction to average 63% and this treatment effect was statistically significantly larger than the average percent reduction in all other treatments except the B500 and C2000 treatments (percent reduction of 40% and 38%, respectively) (Table 1). The U.H. data showed the percent reduction in the B2000 treatments to average 86% and was statistically significantly larger than all the other treatments except the BO treatment (percent reduction of 54%)(Table 2).

Baermann Funnel Results

Both Maui Pine and U. H. Baermann funnel testing showed the B2000 treated plants to have the highest average percent reduction of all the treatments. The Maui Pine data showed this percent reduction to average 93% and was statistically significantly larger than the average percent reduction in the AO, AC, A500, A2000 and BX treatments. The C2000 treatments averaged a percent reduction of 92%, while the C500 and the CO treatments averaged 89%(Table 3). The U.H. data showed the B2000 percent reduction to average 97% and was statistically significantly larger than the AC, A500 and BX treatments. The CO and C500 treatments averaged a reduction of 95%(Table 4).

Phytotoxic Observations

No phytotoxic effect was observed in any of the plants treated during this trial. The last observation was conducted at more than 3 months after application.

Discussion

Both elutriator and Baermann funnel testing by the Maui Pine and U.H. labs indicate the B2000 formulation to be the most effective in controlling reniform nematodes. The B500 formulation showed good efficacy in both U.H. and Maui Pine elutriator testing but was not as effective as the B2000 formulation, indicating increasing efficacy at higher concentrations of ABR. The C2000 formulation consistently was among the most effective treatments and was generally followed by the C500 formulation, indicating an effective formulation (but not as effective as the B formulation) which was also more effective at the higher concentration of ABR. The CO treatment did show good efficacy, but mostly in the Baermann-funnel data.

Conclusion

The data indicate a level of control of reniform nematodes in the B, C and D emulsifier/surfactant formulations, with the B being the most effective. Higher concentrations of ABR generally gave a higher level of control and did not appear to have a phytotoxic effect on the plants treated in this trial.

EXAMPLE 4

Additional Nematicide Formulation

An additional formulation is prepared in a manner similar to that set forth in Example 1 except that a crude cheese extract is used in place of Validase, safflower oil is the oil treated, and white pepper is added as an antimicrobial agent. The adjuvant formulation of detergents and surfactants is as described. The formulation is preferably made with Munster or blue cheese.

The invention claimed is:

1. A clear aqueous microemulsion pesticidal formulation consisting essentially of, as active ingredients
   (a) a saccharide, esterified to at least one monounsaturated $C_{16}$-$C_{20}$ fatty acid to form a complex;
   (b) an anionic surfactant blend;
   (c) nonionic and/or amphiphilic surfactant blend that promotes microemulsion formation; and
   (d) wherein said clear aqueous formulation has a turbidity of less than 3 NTU.

2. The formulation of claim 1 wherein in said microemulsion at least one surfactant comprises polyalkoxy chains.

3. The formulation of claim 2 wherein said polyalkoxy chains are polyethoxy chains.

4. The formulation of claim 1 wherein said fatty acid is oleic acid.

5. The formulation of claim 1 wherein said saccharide is sorbitol.

6. The formulation of claim 1 wherein said fatty acid is derived from a vegetable oil.

7. The formulation of claim 1 wherein said emulsion has a turbidity less than 1 NTU.

8. The formulation of claim 1 wherein the ratio of component (a) to surfactant is about 1:6.5-1:8.5.

9. The formulation of claim 8 wherein the ratio of component (a) to surfactant is 1:7.75.

10. The formulation of claim 1, wherein said formulation further comprises ethoxylated linear alcohols of $C_8$-$C_{11}$.

11. A method for controlling agricultural pests wherein said method comprises applying the formulation of claim 1 to an area in which such control is desired.

* * * * *